(12) United States Patent
Banville et al.

(10) Patent No.: US 10,098,573 B2
(45) Date of Patent: Oct. 16, 2018

(54) ALERTING USERS OF CPR FEEDBACK DEVICE OF DETECTED MAGNETIC INTERFERENCE

(75) Inventors: Isabelle L. Banville, Newcastle, WA (US); Robert Peter Marx, Jr., Kent, WA (US); David Thomas Brown, Lynnwood, WA (US); Richard C. Nova, Seattle, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 1028 days.

(21) Appl. No.: 13/598,508

(22) Filed: Aug. 29, 2012

(65) Prior Publication Data

US 2013/0225972 A1  Aug. 29, 2013

Related U.S. Application Data

(63) Continuation-in-part of application No. 13/250,974, filed on Sep. 30, 2011, now Pat. No. 9,486,390.

(60) Provisional application No. 61/528,869, filed on Aug. 30, 2011, provisional application No. 61/388,461, filed on Sep. 30, 2010.

(51) Int. Cl.
*A61H 31/00* (2006.01)
*A61B 5/11* (2006.01)

(52) U.S. Cl.
CPC .......... *A61B 5/1126* (2013.01); *A61H 31/005* (2013.01); *A61H 31/007* (2013.01); *A61H 2201/5061* (2013.01); *A61H 2201/5064* (2013.01); *A61H 2201/5071* (2013.01); *A61H 2201/5084* (2013.01); *A61H 2201/5097* (2013.01)

(58) Field of Classification Search
CPC .. A61B 5/1126; A61H 31/005; A61H 31/007; A61H 2201/5061; A61H 2201/5097
See application file for complete search history.

(56) References Cited

U.S. PATENT DOCUMENTS

| | | | |
|---|---|---|---|
| 3,804,082 A | | 4/1974 | Tarjan et al. |
| 3,870,038 A | * | 3/1975 | Arblaster ............. A61H 31/008 601/41 |
| 4,228,803 A | * | 10/1980 | Rickards ................ A61N 1/365 607/25 |
| 4,953,305 A | * | 9/1990 | Van Lente ............. G01C 17/38 33/356 |
| 6,306,107 B1 | | 10/2001 | Myklebust et al. |
| 6,937,906 B2 | * | 8/2005 | Terry ....................... A61N 1/37 607/63 |
| 7,220,235 B2 | | 5/2007 | Geheb et al. |
| 2004/0267325 A1 | * | 12/2004 | Geheb ...................... A61B 5/11 607/5 |
| 2006/0015044 A1 | | 1/2006 | Stavland et al. |
| 2007/0276300 A1 | * | 11/2007 | Olson .................. A61H 31/005 601/41 |

(Continued)

*Primary Examiner* — Timothy Stanis
(74) *Attorney, Agent, or Firm* — Lane Powell PC

(57) ABSTRACT

A medical device and/or a method are used by a rescuer who is caring for a patient. The depth of CPR chest compressions is determined, by detecting magnetic fields. An interference is sensed, which is not associated with the CPR chest compressions, but which is superimposed on the detected magnetic fields. Appropriate countermeasures may be taken, if the sensed interference is larger than a threshold.

24 Claims, 10 Drawing Sheets

DEVICE TO MEASURE CPR COMPRESSION DEPTH

(56) References Cited

U.S. PATENT DOCUMENTS

| | | | |
|---|---|---|---|
| 2009/0228240 A1* | 9/2009 | Makela | G01R 31/002 702/185 |
| 2010/0022904 A1 | 1/2010 | Centen | |
| 2010/0228165 A1 | 9/2010 | Centen | |
| 2011/0156700 A1* | 6/2011 | Kariv | G01R 33/007 324/244 |

* cited by examiner

FIG. 1 DEVICE TO MEASURE CPR COMPRESSION DEPTH

*NET DEPTH MEASUREMENT BETWEEN TOP AND BOTTOM MECHANISMS*

$$|r| = \sqrt{I^2 + Q^2}$$
$$\angle r = a\tan 2(I, Q)$$

TETHERED CONNECTION BETWEEN
TOP DEVICE AND BOTTOM DEVICE

COMPONENTS OF TOP DEVICE AND BOTTOM DEVICE WITH REFERENCE SENSOR FOR CPR FEEDBACK

EXAMPLE FEATURES OF BOTTOM DEVICE

ALERTING USERS OF CPR FEEDBACK DEVICE OF DETECTED MAGNETIC INTERFERENCE

CROSS REFERENCE TO RELATED PATENT APPLICATIONS

The present description gives instances of medical devices and methods, the use of which may help overcome problems This patent application claims the benefit of U.S. Provisional Patent Application Ser. No. 61/528,869, entitled "ALERTING USERS OF CPR FEEDBACK DEVICE OF DETECTED MAGNETIC INTERFERENCE," filed on Aug. 30, 2011, the disclosure of which is herein incorporated by reference in its entirety.

This patent application is also a continuation-in-part of U.S. patent application Ser. No. 13/250,974, entitled REFERENCE SENSOR FOR CPR FEEDBAK DEVICE, filed on Sep. 30, 2011, currently pending, which claims the benefit of U.S. Provisional Patent Application Ser. No. 61/388,461, entitled "REFERENCE SENSOR EMBODIMENT FOR CPR FEEDBACK DEVICE," filed on Sep. 30, 2010, the disclosures of which are herein incorporated by reference in their entirety.

FIELD

This invention generally relates to medical devices, and specifically to CPR feedback devices.

BACKGROUND

In humans, the heart beats to sustain life. In normal operation, the heart pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrhythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

During VF, the person's condition deteriorates, because the blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

While basic instructions are helpful, providing feedback to the rescuer during CPR can improve the rescuer's ability to provide effective CPR. Advanced medical devices can actually coach a rescuer who performs CPR. For example, a medical device can issue instructions, and even prompts, for the rescuer to perform CPR more effectively. Sometimes, however, due to an ambient interference, the measurement gathered by a medical device can be skewed, and therefore be rendered unreliable.

To provide effective feedback, an advanced medical device has to be able to measure various components of the administered CPR and provide accurate and precise feedback to a user and/or rescuer. If, for example, magnetic fields are present in the vicinity of a CPR feedback device, which itself also uses a magnetic field, feedback may become altered and unreliable.

BRIEF SUMMARY

The present description gives instances of medical devices and methods, the use of which may help overcome problems and limitations of the prior art.

In one embodiment, a medical device for use by a rescuer who is caring for a patient determines the depth of the CPR chest compressions by detecting magnetic fields. In another embodiment, a method for use by a rescuer who is caring for a patient determines the depth of the CPR chest compressions by detecting magnetic fields. In some embodiments, an interference is sensed, which is not associated with the CPR chest compressions, but which is superimposed on the detected magnetic fields. Appropriate countermeasures may be taken, if the sensed interference is larger than a threshold.

These and other features and advantages of this description will become more readily apparent from the following Detailed Description, which proceeds with reference to the drawings, in which:

DETAILED DESCRIPTION

As has been mentioned, the present description is about medical devices, control systems, software and methods for measuring the depth of Cardio Pulmonary Resuscitation (CPR) chest compressions delivered to the chest of a patient.

Embodiments are now described in more detail.

Figure 1:
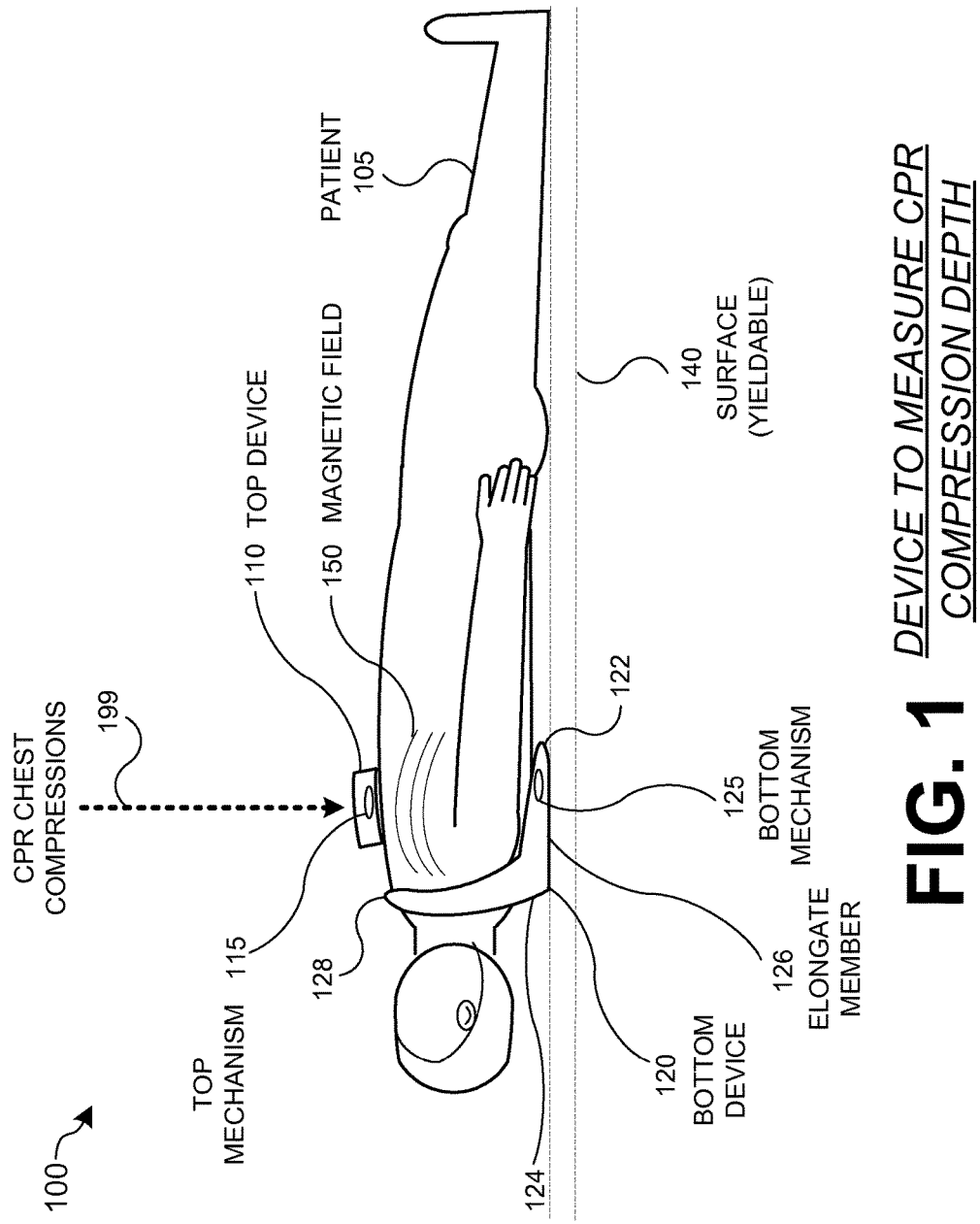
FIG. 1 is a diagram of a scene where a patient is being rescued by being administered CPR chest compressions; and a sample system of a pair of cooperating medical devices are structured to measure the depth of the CPR chest compression according to embodiments.

FIG. 1 is a diagram of a scene 100, where a patient 105 is being rescued by being administered CPR chest compressions 199. A sample system of a pair of cooperating medical devices 110, 120 are structured to measure the depth of CPR compressions 199 according to embodiments. The pair 110, 120 of medical devices includes a top device 110 and a bottom device 120 that work cooperatively to provide values for a net compression depth of CPR chest compressions 199. The cooperating pair works by generating and utilizing a magnetic field 150.

By way of an example, FIG. 1 further depicts a rescue scene 100 where a patient 105 needing CPR is placed face up on a surface 140. The surface 140 may be any type of surface where treatment can be provided. The surface 140 may be rigid, or may not be completely rigid and fixed, and hence, has some yield or flex when force is applied to it. For example, a patient 105 may be placed on a carpet, a padded medical stretcher, a hospital bed, a surface within an ambulance, or any other type of surface that has some yield. The surface 140 may also comprise metal parts and may interfere with the magnetic field or fields generated by the cooperating pair of top device 110 and bottom device 120.

The top device 110 is intended for placement on the chest of the patient 105 and has a top mechanism 115 that is moveable up and down as the chest compressions 199 are delivered to the patient 105. The bottom device 120 includes a generally elongate member 126 having a near end 124 and a distal end 122. A handle 128 is included at the near end 124 that allows a rescuer to grasp and move the bottom device 120. Near the distal end 122, the bottom device includes a bottom mechanism 125. As shown in FIG. 1, the elongate member 126 of the bottom device 120 is structured to be placed between the patient 105 and the surface 140 so that at least a portion of the handle 128 protrudes from under the patient. With this placement, the bottom mechanism 125 is moveable up and down as the CPR chest compressions 199 cause the surface 140 to move up and down. As both the top mechanism 115 and the bottom mechanism 125 are capable of movement during the CPR chest compressions 199, they generate and utilize magnetic field 150 and further calculate a value for a net depth of the compressions of the patient chest with reference to each other.

Figure 2:
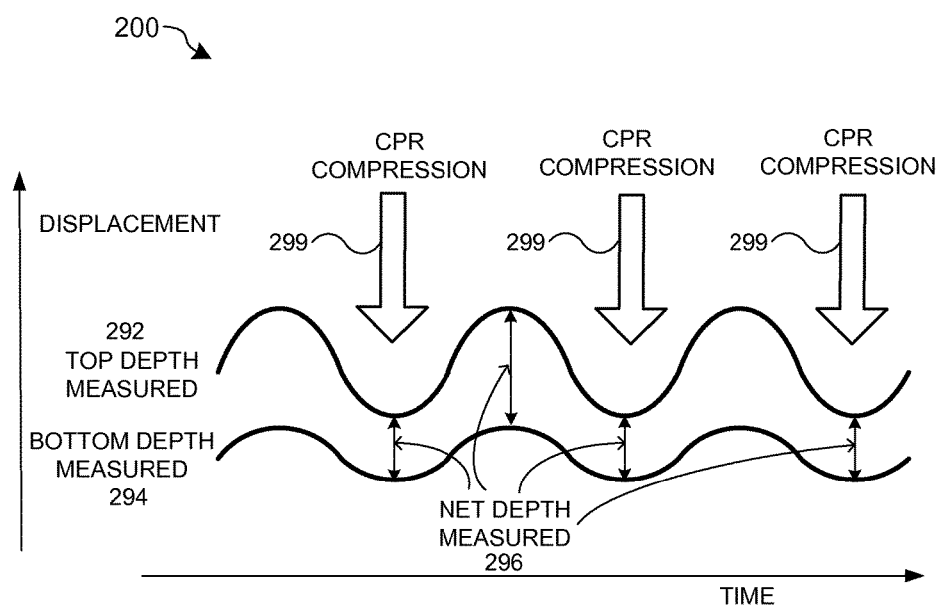
FIG. 2 is a graphical representation of determining net depth measurements during CPR compressions from the cooperating pair of medical devices shown in FIG. 1 according to embodiments.

FIG. 2 is a graphical representation 200 of determining net depth measurements between top 115 and bottom 125 mechanisms from the device shown in FIG. 1 in accordance with one embodiment. The net depth measured 296 is measured in real time, during CPR compressions 299. Referring to FIGS. 1 and 2, a vertical axis represents displacement occurring in a vertical direction during delivery of CPR accurately approximating motion of the chest of the patient 105 and motion of the yieldable surface 140. A horizontal axis represents time. Here, a measured top depth indication line 292 correlates to measurements taken by the top mechanism 115 in the top device 110 and a measured bottom depth indication line 294 correlates to measurements recorded by the bottom mechanism 125 in the bottom device 120. As shown by these indication lines 292, 294 during CPR chest compressions 299, both the top mechanism 115 and the bottom mechanism 125 record changes in displacement due to the force of the compressions. The difference between measured top depth 292 and the measured bottom depth 294 that is recorded during the compressions 299 results in a net depth measurement 296 for the compressions. This net depth measurement 296 accurately reflects the actual depth that the chest of the patient 105 is being compressed during CPR. Since the amount of yield that the surface 140 on which a patient 105 is positioned can vary drastically depending on the surface, the top and bottom depth measurements 292, 294 may vary significantly. However, the difference between these measurements, i.e., the net depth measurement 296, will be relatively consistent for similar chest compression depths.

Figure 3:
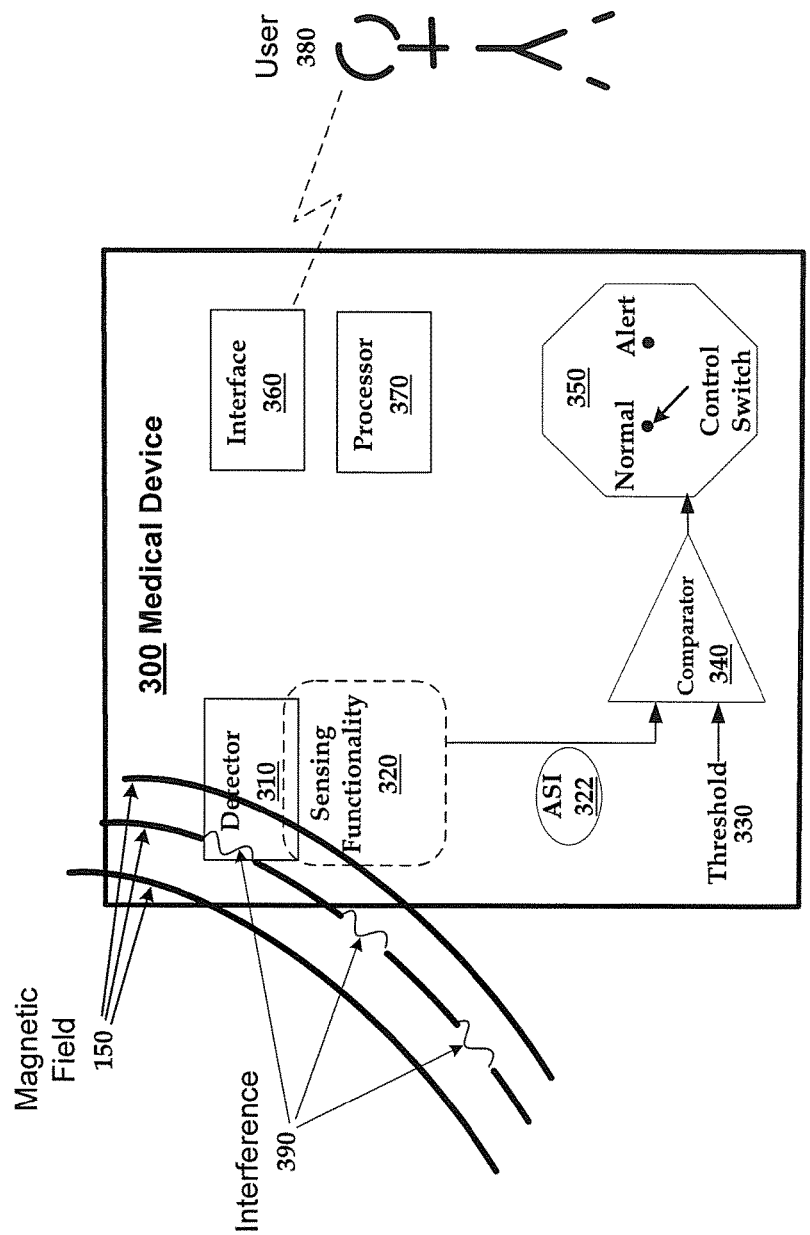
FIG. 3 is a diagram of a medical device configured to respond to ambient magnetic field interference during a CPR event as shown by example in FIG. 1 according to embodiments.

FIG. 3 is a functional block diagram of components of an exemplary medical device 300, in accordance with one embodiment. Device 300 may be a way of implementing either device 110 or device 120 of FIG. 1 according to embodiments.

Device 300 is structured to help measure CPR chest compression depth, and further structured to respond to ambient magnetic field interference during a CPR event. More particularly, device 300 can detect magnetic field 150 of FIG. 1, even though interference 390 is superimposed on field 150. Sources of magnetic field 150 can be either from components of a cooperating medical device, as shown by way of an example in FIG. 1, and which are associated with the CPR chest compressions. Moreover, interference 390 may be superimposed on field 150 from ambient magnetic fields that are not associated with the CPR chest compressions of the medical device 300. The interference 390 may be static or dynamic in nature. In some embodiments, the medical device 300 is capable of detecting interference 390, and/or differentiating interference 390 from field 150, and/or filtering interference 390 from magnetic field 150.

The medical device 300 includes a detector 310, which is suitable for detecting magnetic fields 150 associated with the CPR chest compressions. Device 300 also includes a processor 370 for estimating depths of the CPR chest compressions from the detected magnetic fields 150, and an interface 360 for communicating the estimated depths to a user 380. Device 300 also includes a sensing functionality 320, for sensing whether, in a vicinity of the detector 310, there is interference 390 superimposed on the detected magnetic fields 150, in cases which interference 390 is not associated with the CPR chest compressions. Device 300 also includes a comparator 340 for determining whether an amount ASI 322 of the sensed interference 390 is above a threshold 330. Device 300 moreover includes a control switch 350 that has a normal position and an alert position. In some embodiments, the control switch is thrown from the normal position to the alert position, if it is determined that the amount of the sensed interference is above the threshold. In a further embodiment, the interface 360 notifies the user 380 and/or transmits an error message to another device, such as a device receiving data from the medical device 300. The interface 360 can include visual means, sound means, mechanical, data transmission, and other means as would be apparent to one skilled in the art. Visual means can be displays, lights, sounds. Sound means can be verbal instructions, musical, tone. Mechanical means can include vibration, disabling of the medical device 300. Data transmission means can be wireless such as with the BLUETOOTH wireless standard for exchanging data or WI-FI wireless networking, or wired such as a cable connecting device to a central unit such as physiological vital signs monitor. Detection of interference resulting from the ambient magnetic field interference 390, in yet further embodiment, is captured in the internal data capture, such as a removable media card, and/or the memory of the medical device 300, and transmitted at a time based on situation, emergency, convenience and/or choice. If the medical device 300 determines the source of the magnetic field interference 390, the interface 360 may also communicate this information to the user in a form of a human-perceptible warning via the interface 360 or report, or a machine-perceptible warning. The detector is disabled if the control switch is thrown from the normal position to the alert position and the user is alerted of the disabling by the interface if the control switch is thrown from the normal position to the alert position. Alternatively or additionally, communicating by the interface is disabled if the control switch is thrown from the normal position to the alert position.

In a further embodiment, when the medical device 300 detects a presence of the interference resulting from the ambient magnetic field interference 390, the medical device 300 can notify a user 380. Additionally or alternatively, the medical device 300 can engage and initiate an internally- or externally-invoked algorithm to use the estimated field strength, filter the magnetic field interference 390, and correct, utilize, and process the magnetic field 150 values associated with the CPR chest compressions 199 illustrated, by way of an example, in FIG. 1. When the control switch 350 is thrown from normal to alert position, the medical device 300 can proceed by estimating the depths of the CPR chest compressions and adjust for the sensed interference resulting from the ambient magnetic interference 390. The medical device 300, in yet further embodiment, is capable of providing to the user 380 a report of the type of interference, threshold exceeded, protocol(s) engaged, and corrections or actions made in real-time and/or post-event.

Figure 4:
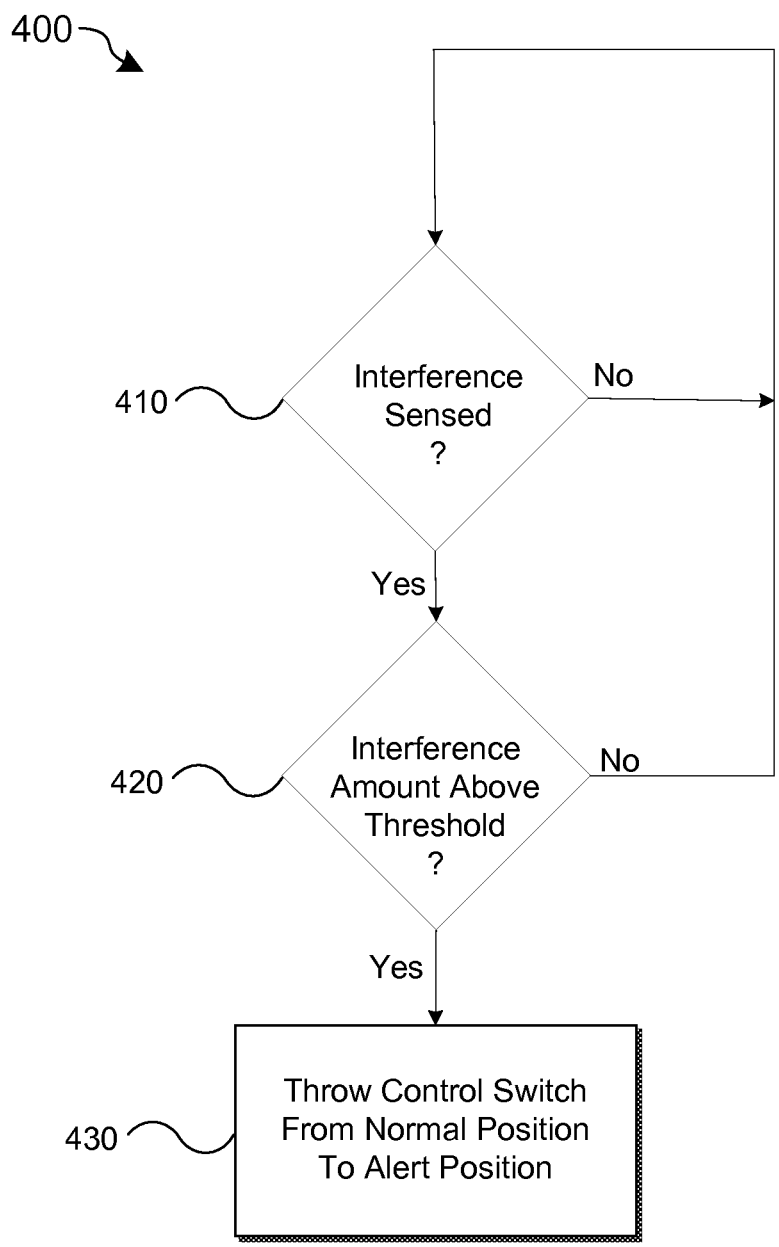
FIG. 4 is a flow diagram of a method for sensing and alerting of ambient magnetic field interference according to embodiments.

FIG. 4 is a flow diagram of a method 400 for a medical device having a detector that is suitable for detecting magnetic fields associated with the CPR chest compressions, a processor for estimating depths of the CPR chest compressions from the detected magnetic fields and a control switch having a normal position and an alert position. The steps of the method 400 include: sensing (410) whether, in a vicinity of the detector, there is interference superimposed on the detected magnetic fields, which interference is not associated with the CPR chest compressions, determining whether an amount of the sensed interference is above a threshold (420), and if so, throwing the control switch from the normal position to the alert position (430).

In one embodiment, the method 400 takes place repetitively, continually or substantially continuously as the detector detects magnetic fields associated with successive ones of the CPR chest compressions. The method checks for sensing of interference (410), such as ambient magnetic field interference, and determines whether the interference is above a predetermined threshold level (420). When above the threshold, the technique invokes alerting of the interference (430). Sensing of the magnetic interference by a sensing functionality and/or differentiating the interference from the magnetic fields associated with the CPR chest compressions is then also continual or substantially continuous, as the detector detects magnetic fields associated with successive ones of the CPR chest compressions.

In a further embodiment, if the control switch is thrown from the normal position to the alert position, the estimated chest compression depths are adjusted for the sensed interference. Further, when the control switch is thrown from the normal position to the alert position a machine- and/or human-perceptible warning is issued to a user and/or a rescuer. The medical device has an interface, such as described in FIG. 3, for communicating the estimated depths to a user and also for issuing a user-perceptible, human and/or machine warning via the interface 360. In a still further embodiment, if the control switch is thrown from the normal position to the alert position, the detector is disabled and the user is alerted of the disabling by the interface. Alternatively or additionally, if the control switch is thrown from the normal position to the alert position, the communicating via the interface is disabled.

Figure 5:
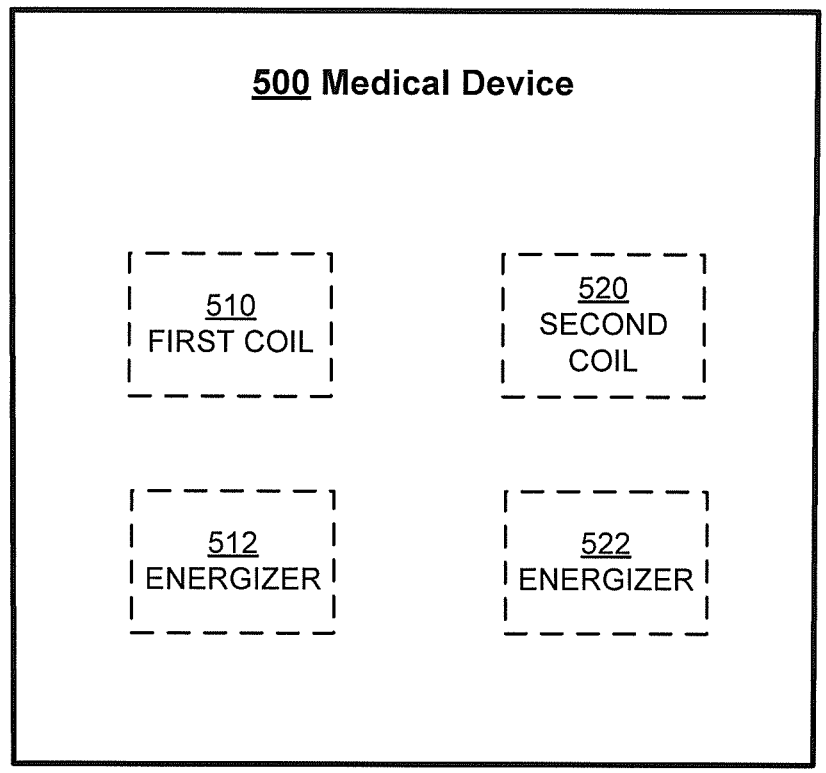
FIG. 5 is a diagram for illustrating different embodiments of a detector and a sensing functionality of the diagram of FIG. 3 according to embodiments.

FIG. 5 is a diagram illustrating an embodiment of medical device 500, which can be one way of implementing device 300. Device 500 comprises an energizer 512, an energizer 522, a first coil 510 and a second coil 520. At least one of coils 510, 520 is a transmitter or transmit coil, and the other is a receiver or receive coil. In one embodiment, the transmitter coil is encased in a housing of device 500, and is capable of transmitting sequentially at a predetermined frequency, thus generating signals. The receive coil may be encased in the same or a separate housing. Such approaches are suitable for the top and bottom devices 110, 120 as illustrated in FIG. 1. The housings can be of any shape as a stand-alone device, or be integrated into another housing that serves other functions, for example a backboard, a monitor, a cell phone, an electrode, a watch, a glove, a vest, an implantable device, a mattress, a bed, a blanket. The power summed from each of the receiver coils, such as the second coil 520, in one embodiment is used to calculate the distance and net depth between the transmitter and receiver coils. In the presence of magnetic interference, a distortion of an expected shape of the dipole field may occur subsequently causing the net depth measurements to become altered and unreliable.

In a different embodiment, the medical device 500 comprises at least two coils, first coil 510 and second coil 520. Sensing is performed by energizing the first coil 510 and the second coil 520, and measuring and comparing current signals induced in the second 520 and first 510 coils respectively by the energizing. Alternately, an impedance of one of both of the coils can be monitored, for how it changes in response to the energizing. The sensing can also be performed by energizing the first and second coils, or the transmit coil with a transmit signal so as to induce a receive signal in the receive coil, detecting a phase delay of the receive signal relative to the transmit signal, and measuring and comparing current signals induced by the energizing. In a further embodiment, at least two transmit coils and two receive coils distinct from the transmit coils are included and sensing is performed by energizing the two transmit coils, and comparing current signals induced in the two receive coils by the energizing.

In one embodiment, at least one of the coils 510 and 520 is wrapped around a ferrous core. Energizer 512 can be a drive coil, which produces an oscillating magnetic field. The strength of the field can be chosen so that it drives the core up to saturation in both directions during a cycle. If no external magnetic field is present, the induced current in the second coil 520 will match the drive current with opposite polarity. However, in the presence of external/ambient magnetic field interference 390, the interference will add to the field associated with the CPR chest compressions, and skew saturation in one direction more than the other direction. This occurrence causes an imbalance between the drive and induced currents, which allows the circuitry to detect the ambient magnetic field interference and then potentially also alert a user. If coils are added so as to cover all three axes, then the presence of any ambient magnetic field interference of sufficient strength, which is above the threshold, can be detected. Such approach can be applied to both conductor and non-conductor based sources of ambient magnetic field interference.

In one embodiment, at initiation, a measurement between pairs of coils and in both directions, meaning tx-to-tx and rx-to-tx is taken. If unperturbed, the measurement in either direction should have matching values. If perturbed by the ambient magnetic interference, the detected signal and measured values would differ however in phase and magnitude, which would then depend on the amount and location of the source of ambient magnetic interference. Additionally or alternatively, if the transmit (tx) coil is energized, the impedance is monitored. If no signal is detected and no impedance shift is detected on the energized coil, then no ambient magnetic interference is present. By way of an example, the applied voltage needs to meet or exceed a threshold to generate an alert. When the interference crosses a predetermined threshold, which is the level that would compromise overall measurement accuracy and/or precision, an alert switch is activated and a user is informed.

Further, a hardware phase discriminator can measure phase differences in the received signal compared and compare it to the transmitted signal. Such technique can be used to, for example, detect the presence of an implantable cardioverter.

Figures 6A, 6B:
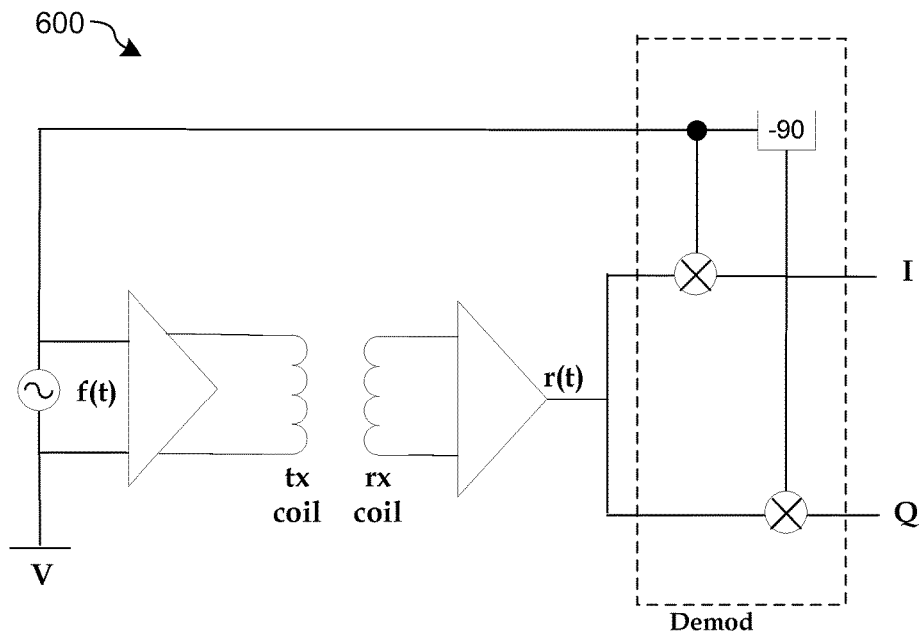
FIG. 6A is a circuit diagram of an embodiment according to the invention.
FIG. 6B is a table illustrating values of parameters of the circuit of FIG. 6A.

FIG. 6A is a circuit diagram 600 that can be used to detect ambient magnetic interference in accordance with an embodiment. In the circuit of FIG. 6, the transmit and receive coils, which can be as shown in FIG. 5, can be coupled as shown and driven as shown. A demodulation technique (Demod) will generate an in-phase signal (I), and quadrature phase signal (Q). Due to a bandwidth used in the implementation of this technique, and a limited sampling frequency, any phase shifts caused by a change in the induced magnetic field generated by a medical device associated with the CPR chest compressions such a presence of a magnetic field interference may skew or even cause a failure to measure relative positioning of the transmit (tx) and receive coil (rx).

FIG. 6B is a table 680. Table 680 illustrates how values of parameters of the circuit of FIG. 6A may be computed. Utilizing the parameters, by way of an example, phase and magnitude of the transmitted signal can be established. The receiver calculates both the in-phase and quadrature components with improved accuracy, allowing for the detection of interference by way of monitoring the phase of the received signal and comparing it with the transmitted signal.

Figure 7:
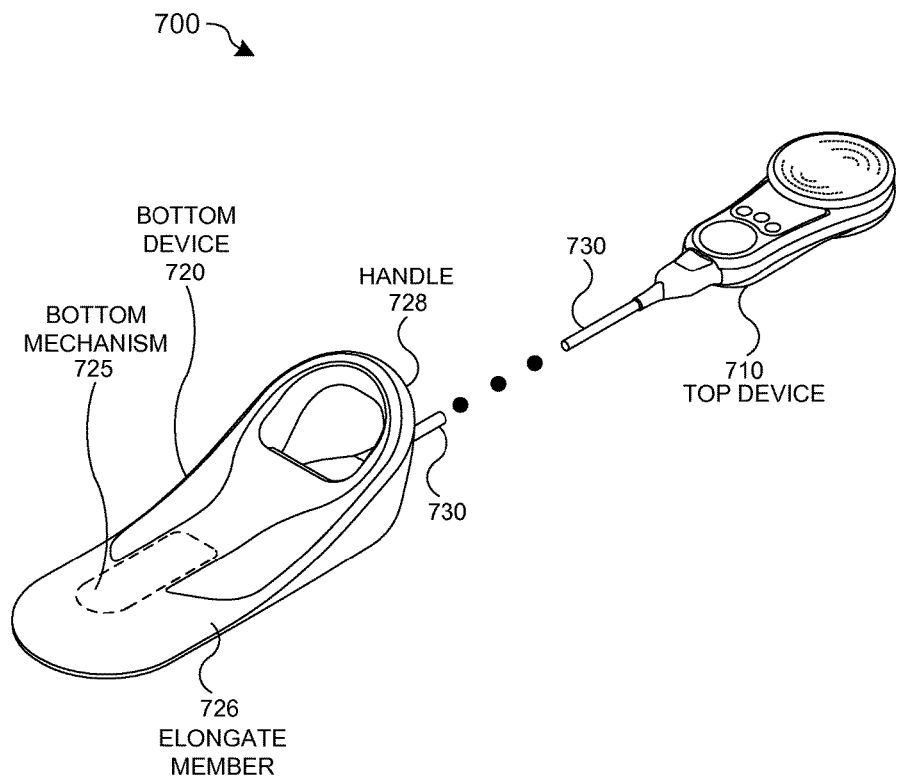
FIG. 7 is an isometric diagram of a cooperating pair of medical devices structured to measure CPR compression depth according to embodiments.

FIG. 7 is an isometric diagram of a cooperating pair of medical devices 710, 720, structured to measure CPR compression depth, and sensing and alerting a presence of ambient magnetic field interference according to embodiments. In particular, FIG. 7 illustrates an example top device 710 that is intended to be placed on the chest of a patient, and an example bottom device 720 that is intended to be placed under a patient during CPR. The bottom device may include an elongate member 726 that has a width that exceeds its cross-sectional height. This shape may make it easy for the bottom device 720 to fit underneath a patient so that a bottom mechanism 725 can accurately measure displacement of a surface during CPR compressions. The bottom device also includes a handle 728, which may include, for instance, a loop, a partial loop, or other shapes for accommodating a hand. This shape of the handle 728 may allow a rescuer to push the bottom device 720 beneath the patient or pull the bottom device from beneath the patient.

In this illustrated embodiment, the top device 710 and the bottom device 720 are physically connected by a tether 730. In some embodiments, the tether 730 may be fixed to each of the top and bottom devices 710, 720. In other embodiments, however, the tether may disconnect from one or both of the top and bottom devices. The tether 730 may simply attach the top device 710 and bottom device 720 so that they do not get separated from one another. However, in other embodiments, the tether 730 may include one or more electrical connectors that transfer data and/or power from one of the top or bottom devices 710, 720 to the other one. In other embodiments, as discussed below, the top and bottom devices 710, 720 may be completely separate and communicate with one another wirelessly or by other means.

Figure 8:
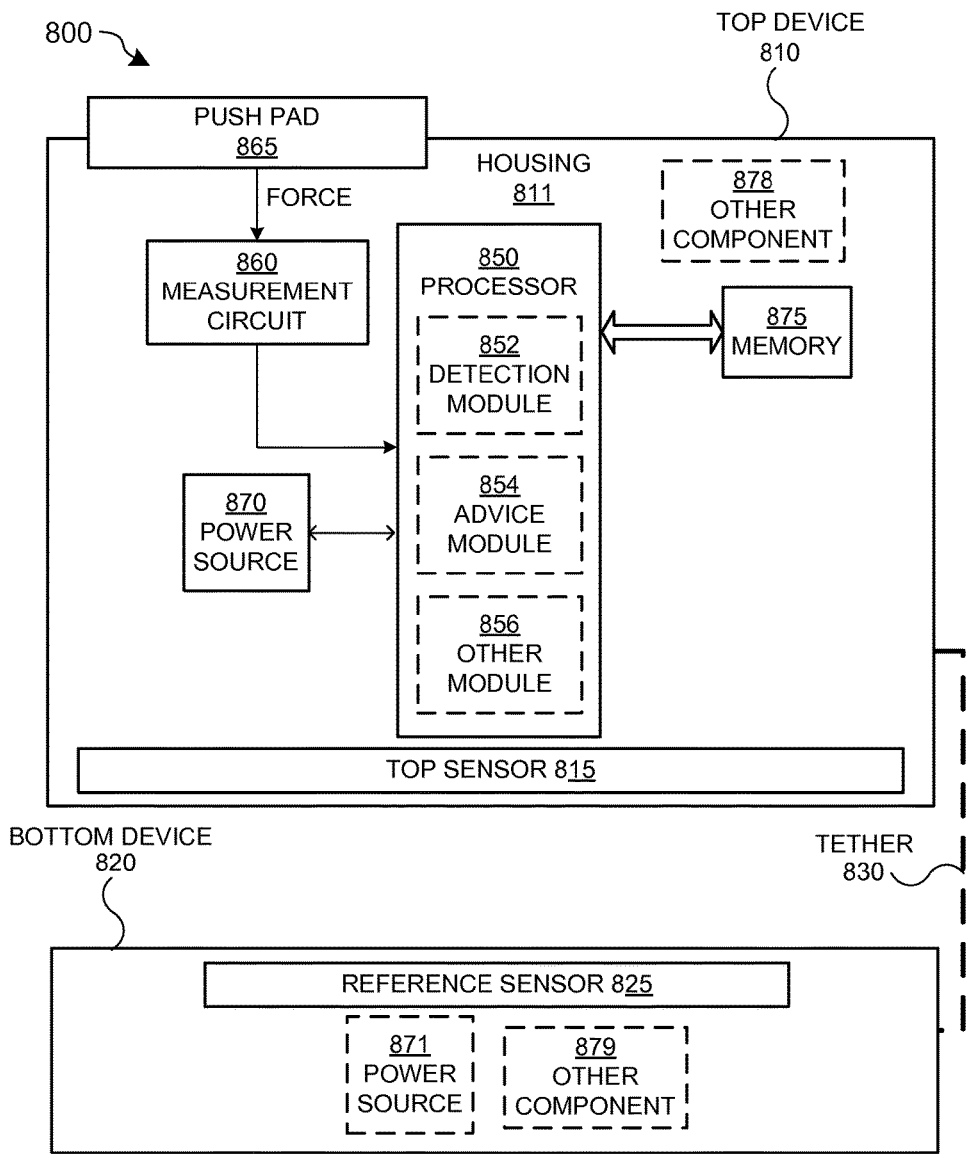
FIG. 8 is a functional block diagram of components of an exemplary device structured to measure CPR compression depth according to embodiments.

FIG. 8 is a functional block diagram of components of an exemplary device 800 structured to measure CPR compression depth according to embodiments. In particular, the device illustrated in FIG. 8 includes a top device 810 and a bottom device 820. The top device 810 includes a processor 850, measurement circuit 860, power source 870, memory 875, and top sensor 815, all of which are encompassed in a housing 811. A push pad 865 is also part of the top device 810 and may protrude at least partially from the housing 811 so as to allow a rescuer to locate and use the push pad. When the top device 810 is placed on the chest of a patient 105 as shown in FIG. 1, and CPR compression is started on the patient, the force applied to the push pad 865 may be measured by the measurement circuit 860 and the resulting measurement may be communicated to the processor 850. The processor may optionally include a detection module 852, an advice module 854, and one or more other modules 856. The force measurements received from the measurement circuit 860 may be detected by the detection module 852 and stored in the memory 875. The top sensor 815 may detect or indicate the displacement or travel distance of the top device 810 during CPR chest compressions. Here, the top sensor 815 may be an embodiment of the top mechanism 115 shown in FIG. 1. The top device may optionally include other components 878, such as a wireless communication module, or other modules.

The bottom device 820 includes a reference sensor 825. The reference sensor 825 may measure or indicate displacement or travel distance of the bottom device 820 during CPR chest compressions. Here, the bottom sensor 825 may be an embodiment of the bottom mechanism 125 shown in FIG. 1. The bottom device may optionally include other components 879, such as a wireless communication module, or other modules. The bottom device may also optionally include a separate power source 871, or may receive power from the power source 870 of the top device 810 through an optional tether 830.

The top device 810 and/or bottom device 820 may include a power switch to power on the respective, or both, devices. The power switches may be represented by the other component modules 878, 879. In some embodiments, the top device 810 and/or bottom device 820 may include a communication port, such as a universal serial bus (USB) port. These communication pots may again be represented by the other component modules 878, 879 in FIG. 8. The communication ports 878, 879 may allow communication between the top device 810 and bottom device 820, or may allow communication with other devices. In some embodiments, the tether 830 may be connected between the communication ports 878, 879 of the top device 810 and bottom device 820 to allow communication and data transfer between the top and bottom devices.

In some embodiments, displacement measurements may be received from both the top sensor 815 and the bottom sensor 825 so that a net displacement depth of the associated CPR compression can be calculated. These measurements may be received by the processor 850 in the top device 810 so that the processor can make the net compression depth calculation. The measurement from the reference sensor 825 may be communicated through the optional tether 830 that connects the top device 810 to the bottom device 820. Alternatively, the measurement from the reference sensor may be transmitted wirelessly from a wireless transceiver 879 in the bottom device to a wireless receiver 878 in the top device 810. A tether 830 may still be present in some embodiments that use a wireless communication protocol, or where no communication channel is required between the top device 810 and the bottom device 820, so that the two parts of the medical device do not get separated. In a further embodiment, sensing and detection of environmental or ambient magnetic field interference is performed by a sensing functionality of other component 878 to the processor 850. The magnetic field interference is then differentiated from estimating depths of the CPR chest compressions and may be neutralized and/or filtered out. In a further embodiment, the interference is communicated to a user through an interface 360 as further illustrated in FIG. 3.

The top sensor 815 and reference sensor 825 may detect or measure displacement by a variety of means. In some embodiments, at least one of the top sensor 815 and the reference sensor 825 establishes a magnetic field for the other, to measure relative position. In other embodiments, the top sensor 815 and the bottom sensor each include an accelerometer. In such an embodiment, acceleration data from the top sensor is compared to acceleration data from the reference sensor 825 to determine a net compression depth of a CPR chest compression.

Figure 9:
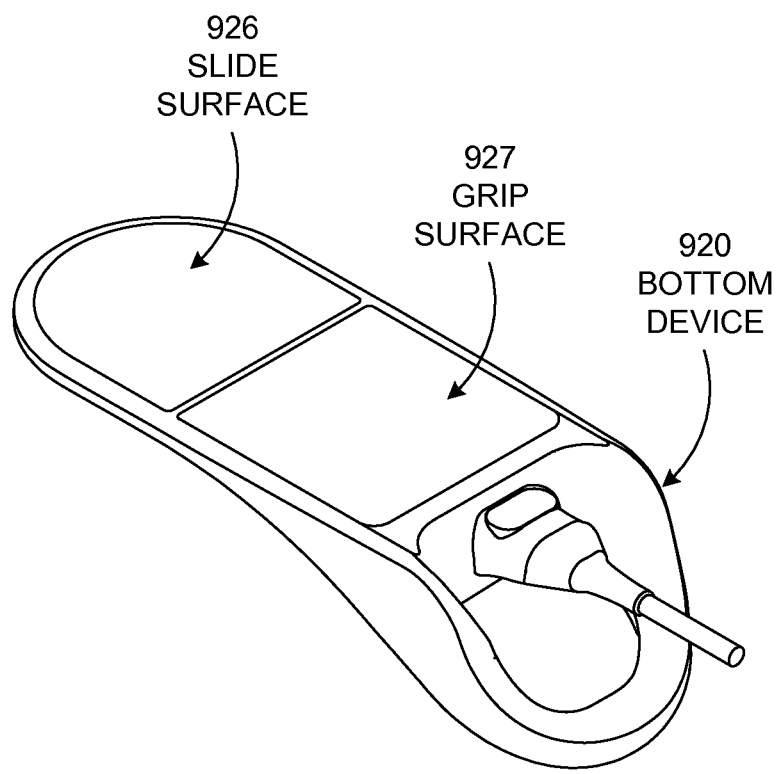
FIG. 9 is an isometric diagram of a bottom device of the cooperating pair of medical devices shown in FIG. 7 showing bottom and side surfaces according to embodiments.

FIG. 9 is an isometric diagram of a bottom device 920 of the cooperating pair of medical devices shown in FIG. 7 showing bottom and side surfaces according to embodiments. In particular, FIG. 9 illustrates that some embodiments of the bottom device 920 include a slide portion 926 and a grip portion 927 on the bottom surface. The slide portion 926 may allow the bottom device to be easily placed under a patient or removed from under a patient, while the grip portion or surface 927 may help keep the bottom device in place under a patient once it is placed and during delivery of CPR. As the grip portion 927 is closer to a handle of the bottom device 920, when a rescuer pulls up on the handle of the bottom device, the grip portion may lose contact with a surface that the patient is lying on thereby allowing the bottom device to be easily inserted or removed by sliding it on the smooth surface of the slide portion 926.

Figure 10:
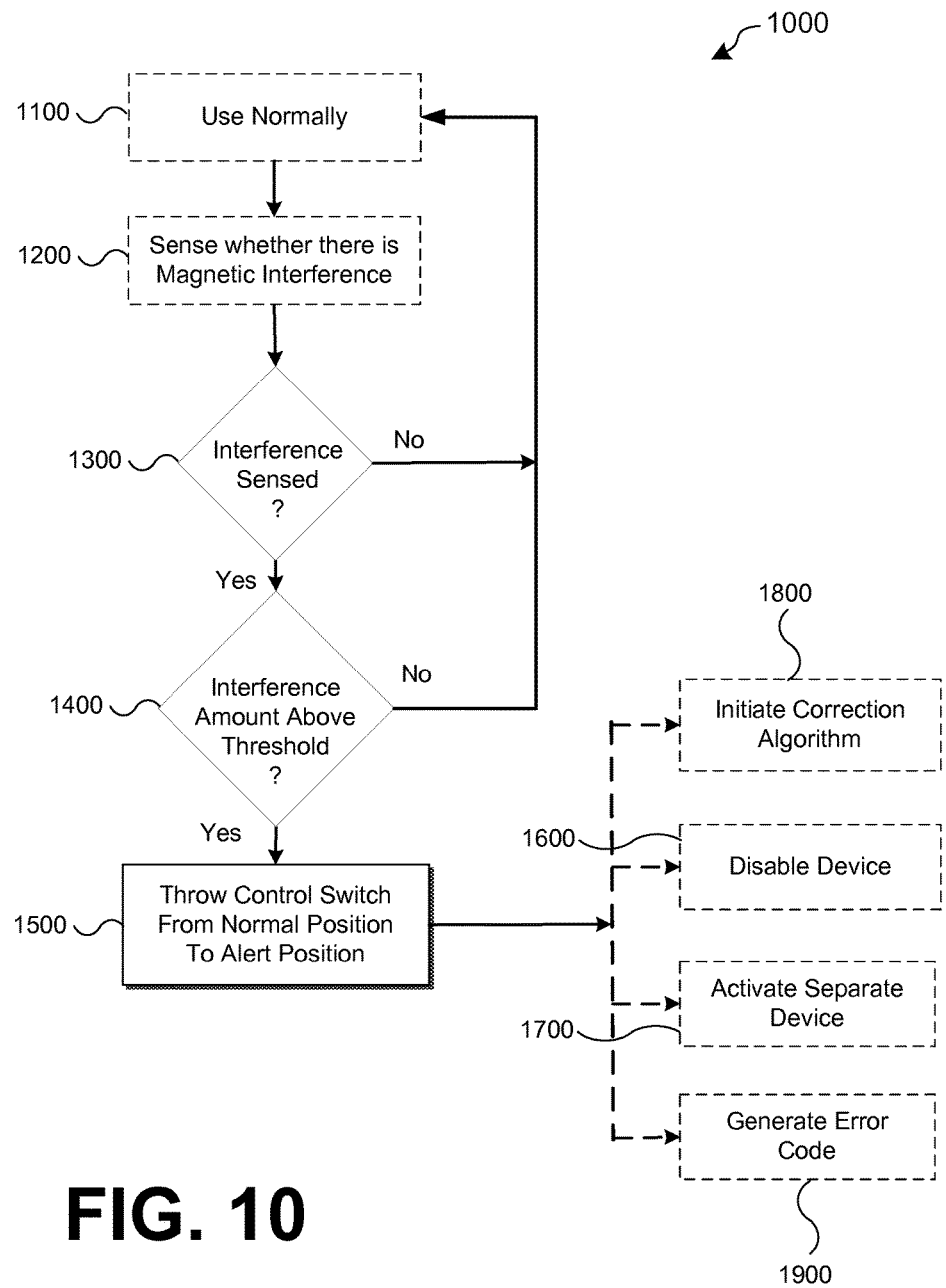
FIG. 10 is a flow diagram of another embodiment of a method for sensing and alerting of ambient magnetic field interference.

FIG. 10 is a flow diagram of another embodiment of a method 1000 for sensing and alerting ambient magnetic field interference. In one embodiment, the method 1000 takes place repetitively, continually or frequently, with the detector detecting magnetic fields associated with successive ones of the CPR chest compressions. The method 1000 senses (1200) whether there is a magnetic interference resulting from ambient magnetic fields interference (1200), which is not associated with CPR chest compressions. If ambient magnetic fields interference is not sensed (1300) or is sensed but below or equal to threshold level (1400), the method will direct to normal use (1100). If however, interference is sensed (1300) and the interference is above a threshold (1400), the control switch from normal position to alert position (1500) and can select from several options, such as to disable device (1600), activate separate device (1700), initiate correction algorithm (1800), and/or generate an error code (1900).

In this description, numerous details have been set forth in order to provide a thorough understanding. In other instances, well-known features have not been described in detail in order to not obscure unnecessarily the description. A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems.

The following claims define certain combinations and subcombinations of elements, features, steps, and/or functions, which are regarded as novel and non-obvious. Additional claims for other combinations and subcombinations may be presented in this or a related document.

What is claimed is:

1. A medical device for communicating to a user information associated with cardiopulmonary resuscitation (CPR) chest compressions performed on a patient in a supine position, the medical device comprising:
    a first sensor configured to be positioned beneath a chest of the patient;
    a second sensor configured to be positioned on the chest of the patient;
    a detector configured to utilize information from the first sensor and the second sensor to detect magnetic fields associated with the CPR chest compressions;
    a processor configured to estimate net depths of the CPR chest compressions between the first sensor and the second sensor from the detected magnetic fields;
    an interface configured to communicate the estimated depths to the user;
    a sensing functionality configured to utilize information from the first sensor and the second sensor to sense whether, in a vicinity of the detector, there is interference, not associated with the CPR chest compressions, that is superimposed on the detected magnetic fields associated with the CPR chest compressions, wherein the first sensor and the second sensor collectively include a coil and the sensing functionality is further configured to energize the coil, to monitor impedance of the coil, and to detect a shift within the monitored impedance of the coil in response to the energizing; and
    a module configured to cause the device to enter an alert mode in response to an amount of the sensed interference being above a threshold.

2. The device of claim 1, in which the sensed interference is static.

3. The device of claim 1, in which the sensed interference is dynamic.

4. The device of claim 1, in which the sensed interference is due to the presence of a conductor in the vicinity of the device.

5. The device of claim 1, in which the first sensor and the second sensor collectively include at least a first coil and a second coil, and in which the sensing functionality is further configured to energize the first and the second coils and measure and compare current signals induced in the second and first coils respectively by the energizing.

6. The device of claim 1, in which the first sensor and the second sensor collectively include at least two transmit coils and two receive coils distinct from the transmit coils, and in which the sensing functionality is further configured to energize the two transmit coils and compare current signals induced in the two receive coils by the energizing.

7. The device of claim 1, in which the first sensor and the second sensor collectively include at least one transmit coil and at least one receive coil, and in which the sensing functionality is further configured to energize the transmit coil with a transmit signal to induce a receive signal in the receive coil, and the sensing functionality is further configured to detect a phase delay of the receive signal relative to the transmit signal.

8. The device of claim 1, in which the sensing functionality includes a hardware phase discriminator.

9. The device of claim 1, in which the processor is further configured to adjust the estimated depths for the sensed interference when the device is in the alert mode.

10. The device of claim 1, in which the medical device is configured to issue a human-perceptible warning to the user when the device is in the alert mode.

11. The device of claim 10, in which the medical device is configured to issue the human-perceptible warning via the interface.

12. The device of claim 1, in which the medical device is configured to disable the detector when the device is in the alert mode.

13. The device of claim 1, in which the interface configured to communicate the estimated depths is disabled when the device is in the alert mode.

14. The device of claim 1, further comprising a bottom device configured to be placed under the chest of the patient, the bottom device having a slide portion and a grip portion on a bottom surface of the bottom device, the grip portion comprising a grip surface configured to contact a support surface and to keep the bottom device under the chest of the patient during delivery of CPR chest compressions to the patient, the first sensor being within the bottom device.

15. The device of claim 1, in which the module configured to cause the device to enter an alert mode comprises:
    a comparator configured to determine whether the amount of the sensed interference is above the threshold; and
    a control switch having a normal position and an alert position, the control switch being thrown from the normal position to the alert position when the determined amount of the sensed interference is above the threshold.

16. A method for a medical device having a detector configured to detect magnetic fields associated with the magnetic fields associated with CPR chest compression chest compressions and a processor configured to estimate depths of the CPR chest compressions from the detected magnetic fields, the method comprising:
    detecting, with the detector, magnetic fields associated with the CPR chest compressions, the detector comprising a first sensor and a second sensor, the first sensor being within a bottom device configured to be placed under a chest of a patient in a supine position on a yieldable surface, the second sensor being configured to be positioned on the chest of the patient;
    estimating net depths of the CPR chest compressions between the first sensor and the second sensor from the detected magnetic fields, excluding yield associated with the yieldable surface under the patient;
    sensing whether, in a vicinity of the detector, there is interference, not associated with the CPR chest compressions, that is superimposed on the detected magnetic fields associated with the CPR chest compressions, further comprising:
        energizing a coil being collectively included in the first sensor and the second sensor;
        monitoring impedance of the coil; and
        detecting a shift within the impedance of the coil in response to the energizing;
    determining whether an amount of the sensed interference is above a threshold; and when the amount of the sensed interference is above the threshold, causing the device to enter an alert mode.

17. The method of claim 16, in which the sensing takes place substantially continuously with the detecting.

18. The method of claim 16, further comprising: repeating the sensing.

19. The method of claim 16, further comprising adjusting the estimated depths for the sensed interference when the device is in the alert mode.

20. The method of claim 16, further comprising issuing a human-perceptible warning to a user when the device is in the alert mode.

21. The method of claim 16, in which the medical device further has an interface for communicating the estimated depths to a user, the method further comprising issuing a human-perceptible warning to the user via the interface when the device is in the alert mode.

22. The method of claim 16, further comprising disabling the detector when the device is in the alert mode.

23. The method of claim 16, in which the medical device further has an interface for communicating the estimated depth to a user, the method further comprising disabling the communicating by the interface when the device is in the alert mode.

24. The method of claim 16, in which the bottom device has a slide portion and a grip portion on a bottom surface of the bottom device, the grip portion comprising a grip surface configured to contact the yieldable surface and to keep the bottom device under the chest of the patient during delivery of CPR chest compressions to the patient.

\* \* \* \* \*